United States Patent
Shimizu et al.

(10) Patent No.: US 10,030,771 B2
(45) Date of Patent: Jul. 24, 2018

(54) GASKET INSERTION METHOD FOR MOUNTING GASKET INSIDE OUTER CYLINDER OF SYRINGE, AND GASKET FOR MOUNTING

(71) Applicant: Terumo Kabushiki Kaisha, Tokyo (JP)

(72) Inventors: Makoto Shimizu, Yamanashi (JP); Hajime Sasamoto, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/009,513

(22) Filed: Jan. 28, 2016

(65) Prior Publication Data

US 2016/0146346 A1    May 26, 2016

Related U.S. Application Data

(63) Continuation of application No. PCT/JP2014/069799, filed on Jul. 28, 2014.

(30) Foreign Application Priority Data

Jul. 29, 2013   (JP) ................ 2013-156367

(51) Int. Cl.
  *F16J 9/20*   (2006.01)
  *A61M 5/315*   (2006.01)
  *B65B 7/28*   (2006.01)

(52) U.S. Cl.
  CPC .............. *F16J 9/20* (2013.01); *A61M 5/315* (2013.01); *B65B 7/2821* (2013.01); *A61M 2207/00* (2013.01); *A61M 2207/10* (2013.01)

(58) Field of Classification Search
  CPC ....... F16J 9/20; A61M 2207/00; A61M 5/315; A61M 2207/10; B65B 7/2821

(Continued)

(56) References Cited

U.S. PATENT DOCUMENTS 3,076,456 A * 2/1963 Hunt, Jr. ............... A61M 5/284
                                                            604/89
3,102,539 A * 9/1963 Goldberg .............. A61M 5/178
                                                           604/236

(Continued)

FOREIGN PATENT DOCUMENTS

DE    10 2005 038 458 A1   2/2007
EP         0 112 574 A     7/1984

(Continued)

OTHER PUBLICATIONS

Extended European Search Report issued in Application No. 14831960.1 dated Jan. 4, 2017.

*Primary Examiner* — Nathan Cumar
(74) *Attorney, Agent, or Firm* — Foley & Lardner LLP (57) ABSTRACT

A gasket insertion method for inserting a gasket into an outer cylinder includes providing an outer cylinder having a base end opening section; providing a gasket having a recessed section that is open at a base end of the gasket and that includes a flat bottom surface; pushing the gasket into a sleeve configured to be inserted into the outer cylinder, by relatively moving an inserter in a tip end direction with respect to the sleeve while a flat tip end surface of a tip end section of the inserter abuts the bottom surface of the recessed section; inserting the sleeve into the outer cylinder through the base end opening section; and arranging the gasket inside the outer cylinder by relatively moving the sleeve in a base end direction with respect to the outer cylinder while maintaining relative axial positions of the outer cylinder, the gasket, and the inserter.

11 Claims, 5 Drawing Sheets

(58) Field of Classification Search
USPC .......................................... 277/436, 300–316
See application file for complete search history.

(56) References Cited

U.S. PATENT DOCUMENTS

| | | | |
|---|---|---|---|
| 2007/0060875 A1* | 3/2007 | Bassarab | A61M 5/2448 604/84 |
| 2007/0175538 A1 | 8/2007 | Rothbauer et al. | |
| 2011/0276005 A1 | 11/2011 | Hioki et al. | |
| 2012/0016314 A1* | 1/2012 | Tachikawa | A61M 5/31515 604/222 |

FOREIGN PATENT DOCUMENTS

| | | | |
|---|---|---|---|
| JP | 59-155264 A | | 9/1984 |
| JP | 2003 290350 | * | 10/2003 |
| JP | 2003-290350 | | 10/2003 |
| JP | 2007-055647 | | 3/2007 |
| JP | 03-940969 | | 7/2007 |
| JP | 2009-504293 | | 2/2009 |
| JP | 2012-120585 | | 6/2012 |
| WO | WO-2010/064667 | | 6/2010 |

* cited by examiner

GASKET INSERTION METHOD FOR MOUNTING GASKET INSIDE OUTER CYLINDER OF SYRINGE, AND GASKET FOR MOUNTING

CROSS-REFERENCE TO RELATED APPLICATIONS

This application is a continuation application filed under 35 U.S.C. § 111(a) claiming the benefit under 35 U.S.C. §§ 120 and 365(c) of PCT International Application No. PCT/JP2014/069799 filed on Jul. 28, 2014, which is based upon and claims the benefit of priority of Japanese Application No. 2013-156367 filed on Jul. 29, 2013, the entire contents of which are hereby incorporated by reference in their entireties.

BACKGROUND OF THE INVENTION

The present disclosure relates to a gasket and a gasket insertion method for mounting a gasket inside an outer cylinder of a syringe.

Conventional methods for inserting a gasket into an outer cylinder in the process of manufacturing syringes and prefilled syringes include: a method of using a sleeve (mechanical capping), and a method of using a vacuum (vacuum capping). In the method of inserting a gasket in a prefilled syringe by using a sleeve, the gasket is first pushed by an inserter from a base end side and is inserted into the sleeve, and the sleeve is inserted to a predetermined position in an outer cylinder filled with a drug solution. Next, when the sleeve is moved toward the base end with respect to the outer cylinder, the diameter of the gasket is increased due to elastic restoring force, and the outer circumferential section of the gasket thereby comes into close contact with the inner circumferential section of the outer cylinder and the gasket is mounted inside the outer cylinder. An insertion method using such a sleeve is disclosed in JP 3940969 B1, for example.

In recent years, prefilled syringes have come to be used for various drug solutions, and depending on the type of drug solution or the prescription, their use for administering a small amount of drug solution to be used up at one time is on the increase. A technique for enabling a stable gasket insertion method regardless of the type of a syringe container or the conditions for filling a drug solution is desired.

SUMMARY OF THE INVENTION

According to a conventional gasket insertion method that uses a sleeve, the axis of a gasket may become inclined with respect to the axis of the sleeve at the time of pushing the gasket by an inserter and inserting the gasket into the sleeve. Particularly, as the diameter of the syringe is reduced, the ratio of the surface area per gasket volume is increased and the frictional resistance is increased, and there is a problem that inclination is more likely to occur at the time of gasket insertion. In this case, the gasket is mounted inside the outer cylinder in an inclined state. This state where the gasket is inclined with respect to an outer cylinder affects the outer appearance of the prefilled syringe, and also increases the sliding resistance between the gasket and the outer cylinder, thereby reducing the operability at the time of use, and especially with respect to the prefilled syringe, this state possibly affects the storage stability of the drug solution that is filled inside.

In view of the problems described above, one object of certain embodiments of present invention is to provide a gasket insertion method and a gasket by which inclination of the gasket with respect to an outer cylinder may be suppressed.

To achieve the above described objects, certain embodiments of the present invention provide a gasket insertion method for inserting the gasket into the outer cylinder provided with a base end opening section, wherein the gasket is provided with a recessed section that is open at a base end of the gasket and that includes a depth in an axial direction of the gasket and a flat bottom surface. The gasket insertion method includes: pushing the gasket into a sleeve that is capable of being inserted into the outer cylinder, by relatively moving an inserter in a tip end direction with respect to the sleeve in a state where a flat tip end surface provided to a tip end section of the inserter and the bottom surface of the recessed section are abutted against each other; inserting the sleeve into the outer cylinder through the base end opening section; and arranging the gasket inside the outer cylinder by relatively moving the sleeve in a base end direction with respect to the outer cylinder while maintaining relative positions of the outer cylinder, the gasket, and the inserter in an axial direction.

According to the gasket insertion method described above, the bottom section of the recessed section provided to the gasket is flat, and also the tip end surface of the inserter for pushing the gasket is flat. Accordingly, inclination of the gasket with respect to the sleeve at the time of the gasket being pushed and inserted by the inserter into the sleeve may be suppressed. Therefore, the gasket may be arranged inside the outer cylinder in a state where the inclination of the gasket with respect to the outer cylinder is suppressed.

In the gasket insertion method described above, an inner diameter of the recessed section may be substantially constant along substantially an entire length in a depth direction.

According to the above, the inner circumferential surface of the recessed section whose inner diameter is constant in the depth direction is supported by the outer circumferential surface of the tip end section of the inserter, and thus inclination of the gasket at the time of insertion of the gasket into the sleeve may be effectively suppressed.

In the gasket insertion method described above, a ratio of an inner diameter of the recessed section to an outer diameter of the gasket may be 30% or more, and a ratio of the outer diameter of the tip end section of the inserter to the inner diameter of the recessed section may be 60% or more.

According to the above, the tip end section of the inserter to be inserted into the recessed section of the gasket is relatively thick, and the gap between the outer circumferential surface of the tip end section of the inserter and the inner circumferential surface of the recessed section is small. Accordingly, inclination of the gasket at the time of insertion of the gasket into the sleeve may be effectively suppressed.

In the gasket insertion method described above, a plurality of circular ribs may be formed on an outer circumferential section of the gasket while being spaced apart in the axial direction of the gasket, and a difference between an outer diameter of the circular rib and an outer diameter of a valley section that is formed between adjacent circular ribs may be 0.7 mm or more, or a ratio of the outer diameter of the valley section to the outer diameter of the circular rib may be 90% or less.

According to the above, inclination of the gasket may be suppressed in spite of the sliding resistance between the gasket and the outer cylinder.

In the gasket insertion method described above, of the plurality of circular ribs, the circular rib that is most on a tip end side may be provided on a tip end side than the bottom surface, and of the plurality of circular ribs, the circular rib that is most on a base end side may be provided on a base end side than the bottom surface.

According to the above, the circular ribs are provided at respective positions on the tip end side and the base end side with respect to the position (bottom surface) at which a pushing force from the inserter acts on the gasket. Accordingly, inclination of the gasket at the time of insertion of the gasket into the sleeve may be even more effectively suppressed.

Also, the present invention provides a gasket to be inserted in an outer cylinder in a slidable manner, the gasket including: a gasket main body including a tip end and a base end; a recessed section that is open at the base end of the gasket main body, and that has a depth in an axial direction of the gasket main body; and a plurality of circular ribs that are provided on an outer circumferential section of the gasket main body, and that are formed being spaced apart in the axial direction of the gasket main body, wherein the recessed section includes a flat bottom surface, and a difference between an outer diameter of the circular rib and an outer diameter of a valley section that is formed between adjacent circular ribs is 0.7 mm or more, or a ratio of the outer diameter of the valley section to the outer diameter of the circular rib (32) is 90% or less.

According to the gasket described above, the bottom section of the recessed section provided to the gasket is flat, and also the tip end surface of the inserter for pushing the gasket is flat. Accordingly, inclination of the gasket with respect to the sleeve at the time of the gasket being pushed and inserted by the inserter into the sleeve may be suppressed. Therefore, the gasket may be arranged inside the outer cylinder in a state where the inclination of the gasket with respect to the outer cylinder is suppressed.

In the gasket described above, of the plurality of circular ribs, the circular rib that is farthest on a tip end side may be provided on a tip end side relative to the bottom surface, and of the plurality of circular ribs, the circular rib that is most on a base end side may be provided on a base end side than the bottom surface.

According to the configuration described above, the circular ribs are provided at respective positions on the tip end side and the base end side with respect to the position (bottom surface) at which a pushing force from the inserter acts on the gasket. Accordingly, inclination of the gasket at the time of insertion of the gasket into the sleeve may be even more effectively suppressed.

According to the gasket insertion method and the gasket of certain embodiments of the present invention, inclination of the gasket with respect to the outer cylinder may be suppressed.

DETAILED DESCRIPTION

Hereinafter, embodiments of a gasket insertion method and a gasket according to the present invention will be described with reference to the appended drawings.

Figure 1:
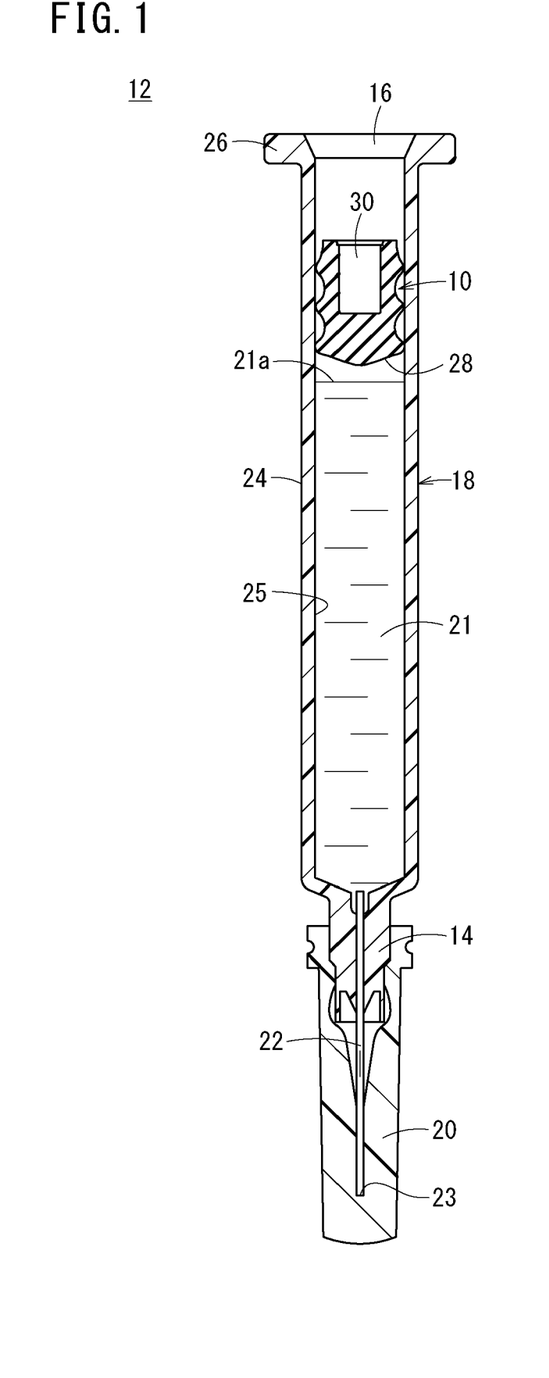
FIG. 1 is a longitudinal cross-sectional diagram illustrating an example configuration of a prefilled syringe.

FIG. 1 is a longitudinal cross-sectional diagram illustrating an example configuration of a prefilled syringe 12 provided with a gasket 10 according to an embodiment of the present invention. The prefilled syringe 12 includes a cylindrical outer cylinder 18 having a cylinder tip section 14 and a base end opening section 16, a cap 20 for sealing the cylinder tip section 14, a drug solution 21 filling the outer cylinder 18, and the gasket 10 which is capable of sliding inside the outer cylinder 18.

The prefilled syringe 12 is formed as a syringe with a needle having a needle 22 fixed at the cylinder tip section 14. Additionally, the prefilled syringe 12 may be provided without the needle 22 (for example, the prefilled syringe may be configured such that a needle is attached before administration by Luer lock fitting or the like).

An inner space section 25 is formed inside an outer cylinder main body 24 forming a trunk section of the outer cylinder 18. The inner space section 25 is filled with the drug solution 21. The cylinder tip section 14 protrudes from a tip end section of the outer cylinder main body 24 in the tip end direction while having its diameter reduced in relation to the outer cylinder main body 24. A base end section of the hollow needle 22 having a sharp needle tip 23 at its tip is fixed to the cylinder tip section 14. A flange section 26 protruding outward is provided to the base end of the outer cylinder main body 24. The base end opening section 16 is formed on the inside of the flange section 26.

The outer cylinder main body 24 is a cylindrical body formed of a transparent or a semi-transparent material which has low oxygen permeability and water vapor permeability as necessary. As the material for forming the outer cylinder main body 24, various resins may be used, such as polypropylene, polyethylene, polystyrene, polyamide, polycarbonate, polyvinyl chloride, poly(4-methyl-pentene-1), acrylic resin, acrylonitrile-butadiene-styrene copolymer, polyester such as polyethylene terephthalate, and cyclic polyolefin. Among these, resins such as polypropylene and cyclic polyolefin are desirable from the standpoint of facility in molding and heat resistance. Alternatively, a metal such as stainless steel or aluminum may be used.

The size of the prefilled syringe 12 is not particularly limited, but the inner diameter of the outer cylinder main body 24 may be from about 4.6 mm to 32.4 mm, according to use. Furthermore, in the present application, a prefilled syringe 12 with a small diameter is desirable, and more preferably, the outer cylinder main body 24 with a small diameter whose inner diameter is about 4.6 mm to about 14.8 mm, or even more preferably, about 4.6 mm to about 6.6 mm is selected.

A cap 20 is formed to have a bottomed cylindrical shape whose base end side is open, and is formed from an elastic material. The needle tip 23 of the needle 22 pierces a tip end section of the cap 20 in a state where the cap 20 is mounted on the outer cylinder 18. The tip end opening of the needle 22 is thereby sealed, and a liquid-tight state in which the drug solution 21 does not leak from the tip end opening is maintained in a state before use when the cap 20 is mounted on the cylinder tip section 14.

As the material for forming the cap 20, various rubber materials may be used, such as natural rubber, butyl rubber, isoprene rubber, butadiene rubber, styrene-butadiene rubber, and silicone rubber, various thermoplastic elastomers based on polyurethane, polyester, polyamide, olefin, and styrene, and a mixture thereof.

As the drug solution 21, various drug solutions may be used, such as injections for correcting electrolyte imbalance such as sodium chloride and potassium lactate, vitamin compounds, vaccines, antibiotic injections, steroid injections, insulins, therapeutic antibodies, proteolytic enzyme inhibitors, fat emulsions, various protein preparations, anticancer agents, anesthetic agents, stimulants, drugs, and various diagnostic agents.

The gasket 10 is inserted inside the outer cylinder 18. A tip end surface 28 of the gasket 10 has a tapered shape which becomes thinner toward the tip end. At an orientation where the cylinder tip section 14 is on the lower side, the tip end surface 28 of the gasket 10 is separated from a liquid surface 21a of the drug solution 21. In other words, at an orientation where the cylinder tip section 14 is on the lower side, a space of a predetermined volume is formed between the liquid surface 21a of the drug solution 21 and the tip end surface 28 of the gasket 10. The pressure in the space is approximately the same as the atmospheric pressure, and is effective for slidability and storage stability at the time of use. Alternatively, the tip end surface 28 of the gasket 10 may be in contact with the drug solution 21 at an orientation where the cylinder tip section 14 faces downward.

Figure 2:
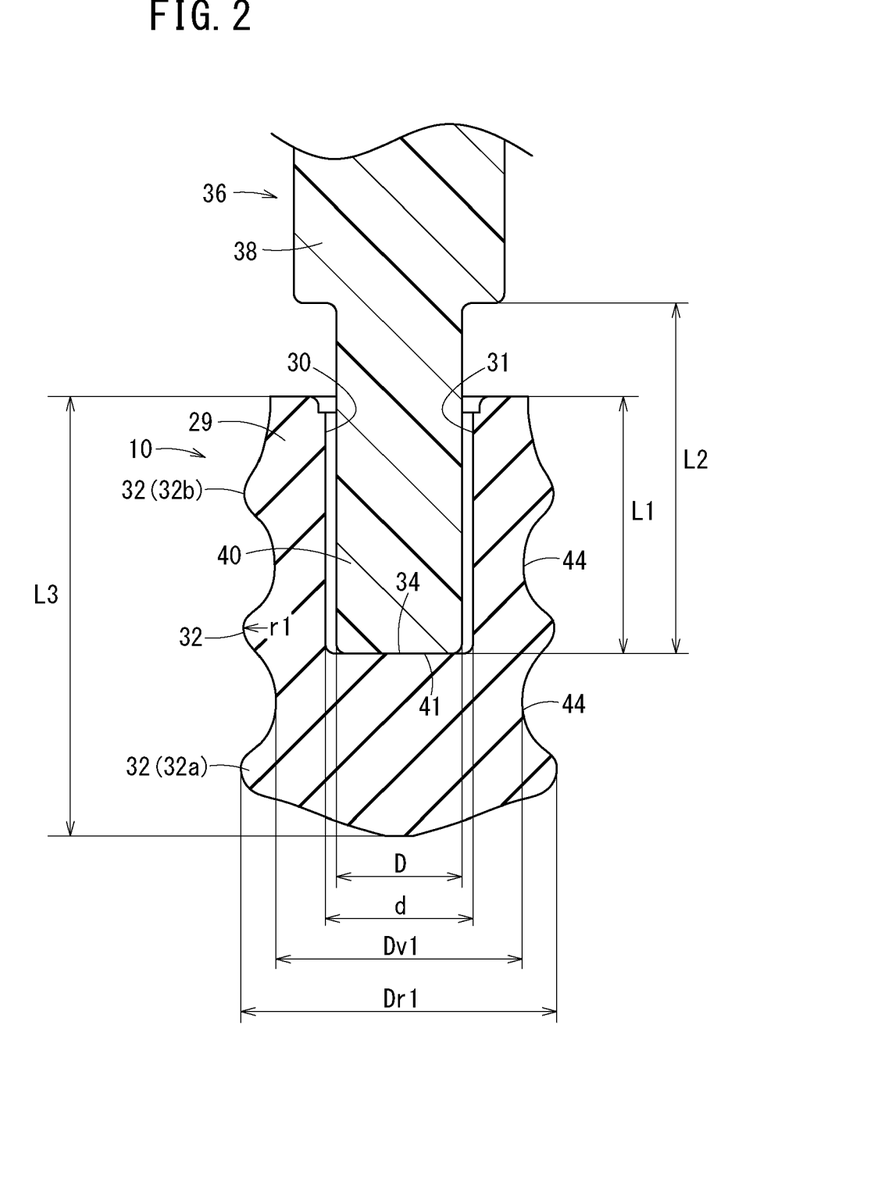
FIG. 2 is a longitudinal cross-sectional diagram of a gasket according to an embodiment of the present invention, and a tip end section of an inserter that is used to insert the gasket into an outer cylinder.

FIG. 2 is a longitudinal cross-sectional diagram of the gasket 10, and a tip end section 40 of an inserter 36 that is used to insert the gasket 10 into the outer cylinder 18. As illustrated in FIG. 2, the gasket 10 is provided with a recessed section 30 and circular ribs 32. Specifically, the gasket 10 includes a gasket main body 29 having a tip end and a base end, the recessed section 30, which is open on the base end side of the gasket main body 29, and a plurality of circular ribs 32 provided on the outer circumferential section of the gasket main body 29. As a whole, the gasket 10 has a substantially circular cylinder shape.

The tip end section of a plunger, not illustrated, may be fitted into the recessed section 30 of the gasket 10. According to the present illustrated example, an inner circumferential section 31 of the recessed section 30 has a smooth circular cylindrical surface. Additionally, an internal thread may be formed on the inner circumferential section 31 of the recessed section 30, and the internal thread may be screwed with an external thread formed to the tip end section of the plunger, not illustrated, or fitting may be performed by recesses and protrusions, for example.

The recessed section 30 has a depth along the axial direction of the gasket main body 29, and also includes a flat bottom surface 34. The bottom surface 34 is formed substantially perpendicularly with respect to the axial direction of the gasket main body 29. In the present example illustrated, an inner diameter d of the inner circumferential section 31 (inner surface) of the recessed section 30 is substantially constant along the entire length along the depth direction of the recessed section 30. Additionally, the part connecting the bottom surface 34 and the inner circumferential section 31 may be curved in an arc shape, or may be inclined in a tapered shape.

In the following, the dimension of each section of the gasket 10 will be described, and if not particularly specified, the dimension in the natural state (a state where no external force is applied, and where there is no elastic deformation) is indicated.

The gasket 10 is set according to the diameter of the outer cylinder main body 24 and the use state, but in the case of being inserted into the outer cylinder main body 24 described above, basically, its total length (L3) is selected from between 5.0 mm and 15.0 mm, and its outer diameter (Dr1) from between 4.8 mm and 33.4 mm. In this case, a depth (the length along the axial direction of the gasket 10) L1 of the recessed section 30 is, for example, between 1.0 mm and 12.0 mm, or more preferably, between 1.0 mm and 9.0 mm, or even more preferably, between 1.5 mm and 9.0 mm, or even more preferably, between 1.5 mm and 7.0 mm. The inner diameter d of the recessed section 30 is, for example, between 1.6 mm and 32.4 mm, or more preferably, between 1.6 mm and 8.2 mm, or even more preferably, between 2.0 mm and 8.2 mm, or even more preferably, between 2.2 mm and 2.8 mm.

The inserter 36 is a long, thin stick-shaped member that is used at the time of inserting the gasket 10 into the outer cylinder 18 in the manufacturing process of the prefilled syringe 12. The outer diameter of the inserter 36 is smaller than the inner diameter of a sleeve 46 described later. Accordingly, the inserter 36 may be inserted into the sleeve 46.

The inserter 36 includes a trunk section 38, and a tip end section 40 which is extending from the tip end of the trunk section 38 and whose diameter is reduced in relation to the trunk section 38. The tip end section 40 is inserted into the recessed section 30 of the gasket 10 at the time when the gasket 10 is pushed by the inserter 36 in the process of insertion of the gasket 10 into the outer cylinder 18. An outer diameter D of the tip end section 40 is substantially constant along the axial direction. The tip end section 40 includes a flat tip end surface 41. The tip end surface 41 is a surface that is perpendicular with respect to the axial direction of the inserter 36. The tip end surface 41 is the part that abuts against the bottom surface 34 of the recessed section 30 of the gasket 10 at the time when the gasket 10 is pushed by the inserter 36 in the process of insertion of the gasket 10 into the outer cylinder 18.

A length L2 of the tip end section 40 is adjusted according to the dimension of the gasket 10, but is longer than the depth L1 of the recessed section 30. The length L2 of the tip end section 40 is, for example, between 3.0 mm and 15.0 mm, and preferably, it is between 3.0 mm and 10.0 mm, or even more preferably, between 3.5 mm and 7.5 mm. The outer diameter D of the tip end section 40 is smaller than the inner diameter d of the recessed section 30. The outer diameter D of the tip end section 40 is, for example, between 1.28 mm and 31.7 mm, and preferably, it is between 1.28 mm and 7.6 mm, or more preferably, between 1.8 mm and 2.4 mm. To reduce the gap between the inner circumferential section 31 of the recessed section 30 and the outer circumferential surface of the tip end section 40, the ratio of the outer diameter D of the tip end section 40 of the inserter 36 to the inner diameter d of the recessed section 30 is 60% or more, or more preferably, 80% or more. Alternatively, the difference between the inner diameter d of the recessed section 30 and the outer diameter D of the tip end section 40 is 0.75 mm or less, or more preferably, 0.65 mm or less.

At the gasket 10, a plurality of circular ribs 32 are arranged spaced apart in the axial direction of the gasket 10. Each circular rib 32 extends in the circumferential direction in the range of 360°, at the outer circumferential section of the gasket main body 29. A valley section 44 is formed between adjacent circular ribs 32. In the present embodiment, three circular ribs 32 are provided. A circular rib 32a, which is farthest on the tip end side, is provided on the tip end side relative to the bottom surface 34. A circular rib 32b, which is farthest on the base end side, is provided on the base end side than the bottom surface 34. Additionally, the number of circular ribs 32 may be two, or four or more.

Each circular rib 32 is in close contact with the inner circumferential surface of the outer cylinder 18 in a state where the gasket 10 is inserted inside the outer cylinder 18. The gasket 10 may thereby slide inside the outer cylinder 18 in a liquid-tight manner.

The outer diameter Dr1 of the circular rib 32 is set according to the inner diameter of the outer cylinder 18 and the outer diameter of the gasket 10, but is, for example, between 4.8 mm and 33.4 mm, and preferably, it is between 4.8 mm and 15.5 mm, or more preferably, between 5.05 mm and 15.5 mm, or even more preferably, between 5.05 mm and 5.45 mm. An outer diameter Dv1 of the valley section 44 is, for example, between 3.6 mm and 32.3 mm, and preferably, it is between 3.6 mm and 13.8 mm, or more preferably, between 4.0 mm and 13.8 mm, or even more preferably, between 4.0 and 4.4 mm. The difference between the outer diameter Dr1 of the circular rib 32 and the outer diameter Dv1 of the valley section 44 is 0.7 mm or more, and preferably, it is 1 mm or more. Alternatively, the ratio of the outer diameter Dv1 of the valley section 44 to the outer diameter Dr1 of the circular rib 32 is 90% or less, and preferably, it is 82% or less. For example, in the case where the outer diameter Dr1 of the circular rib 32 is set to 5.25 mm, and the outer diameter Dv1 of the valley section 44 is set to 4.2 mm, the difference between the outer diameter Dr1 of the circular rib 32 and the outer diameter Dv1 of the valley section 44 is 1.05 mm. Also, in this case, the ratio of the outer diameter Dv1 of the valley section 44 to the outer diameter Dr1 of the circular rib 32 is 80%. Also, a curvature of radius r1 at a crown section of the circular rib 32 is, for example, between 0.1 mm and 1.0 mm, and preferably, it is between 0.2 mm and 0.8 mm. Furthermore, a straight section may be provided as necessary at the center of the crown section of the circular rib 32, and its range is, for example, between 0.05 mm and 0.35 mm, and preferably, it is between 0.1 mm and 0.2 mm.

As the materials for forming the gasket 10, those that are illustrated as the materials for forming the cap 20 may be cited, for example. The gasket 10 may have a coating for reducing the sliding resistance formed on the outer surface of the base material of the gasket 10. As such a coating, there may be used fluorine-based resins such as polytetrafluoroethylene (PTFE), tetrafluoroethylene-perfluoroalkylvinyl ether copolymer resin (PFA), ethylene tetrafluoride-propylene hexafluoride copolymer (FEP), polychlorotrifluoroethylene (PCTFE), and polyvinylidene difluoride (PVDF), silicon-based resins such as a silicone polymer coating formed of a liquid coating composed mainly of non-reactive silicone oil, polyparaxylylene, and diamond-like carbon.

The gasket 10 according to an embodiment of the present embodiment is basically formed in the manner described above. In the following, operations and effects of the gasket 10 will be described in relation to the gasket insertion method according to an embodiment of the present invention. In the following, each step, in the manufacturing process of the prefilled syringe 12 illustrated in FIG. 1, for inserting the gasket 10 into the outer cylinder 18 will be specifically described.

Figure 3A:
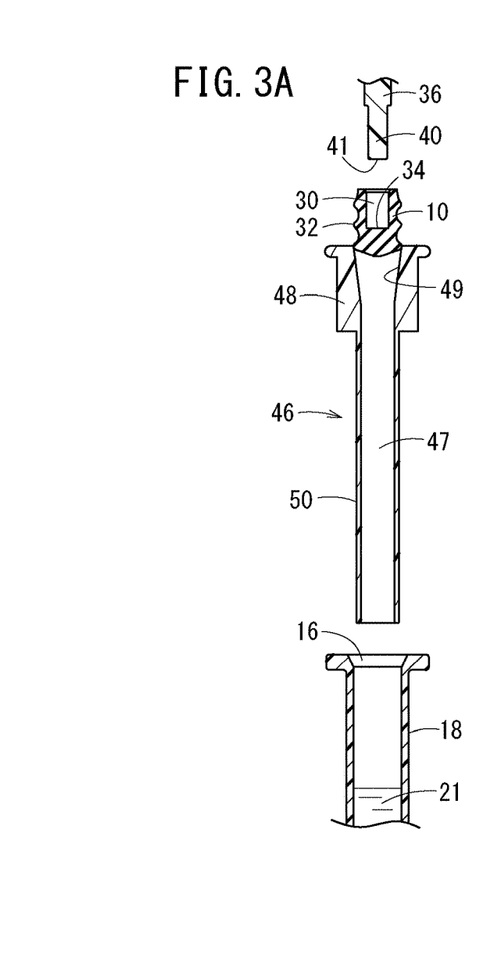
FIG. 3A is a first diagram describing a gasket insertion method according to an embodiment of the present invention.

In FIG. 3A, the outer cylinder 18 is held by a holder, not illustrated, at an attitude where the cylinder tip section 14 (see FIG. 1) faces downward, and the outer cylinder 18 is filled with the drug solution 21. Additionally, the cylinder tip section 14 and the needle 22 are sealed by the cap 20, and are maintained in a liquid-tight manner so that the drug solution 21 does not leak from below.

Also, the sleeve 46 is arranged above the outer cylinder 18, on the same axis as the outer cylinder 18. The sleeve 46 may be moved, by a first moving mechanism not illustrated, in the vertical direction while maintaining the co-axial state in relation to the outer cylinder 18. The sleeve 46 is a tube that can be inserted into the outer cylinder 18. The gasket 10 may be inserted into an inner space 47 of the sleeve 46.

Specifically, the sleeve 46 includes a base section 48, and an insertion section 50 extending downward (in the tip end direction) from the base section 48. An inner circumferential section of the base section 48 is a tapered section 49 whose inner diameter becomes smaller on the lower side. The insertion section 50 is a hollow circular cylinder which is thinner than the base section 48 and is appropriately thin-walled, and which as an outer diameter allowing insertion into the outer cylinder 18. The outer diameter of the insertion section 50 is smaller than the inner diameter of the outer cylinder 18. In FIG. 3A, a tip end section of the gasket 10 is inserted in a base end opening of the base section 48 of the sleeve 46. According to such a structure, the gasket 10 is uniformly compressed in the circumferential direction by the tapered section 49 at the time of being inserted into the inner space 47, and smooth entry into the insertion section 50 with a small inner diameter is enabled.

Furthermore, in FIG. 3A, the inserter 36 is arranged above the sleeve 46, on the same axis as the sleeve 46, with the tip end section 40 facing downward. Therefore, in FIG. 3A, the outer cylinder 18, the sleeve 46, and the inserter 36 are arranged next to one another on the same axis. The inserter 36 may be moved, by a second moving mechanism not illustrated, in the vertical direction while maintaining the co-axial state in relation to the sleeve 46.

When each member is arranged in the manner illustrated in FIG. 3A, the gasket 10 is then pushed into the sleeve 46 by the inserter 36 being moved in the tip end direction with respect to the sleeve 46 in a state where the tip end surface 41 of the tip end section 40 and the bottom surface 34 of the recessed section 30 are abutted against each other (a pushing step). Also, the sleeve 46 is inserted into the outer cylinder 18 through the base end opening section 16 (an insertion step). The pushing step and the insertion step may be performed in parallel in time, or the insertion step may be performed after the pushing step, or the steps may be performed in reverse order.

Figure 3B:
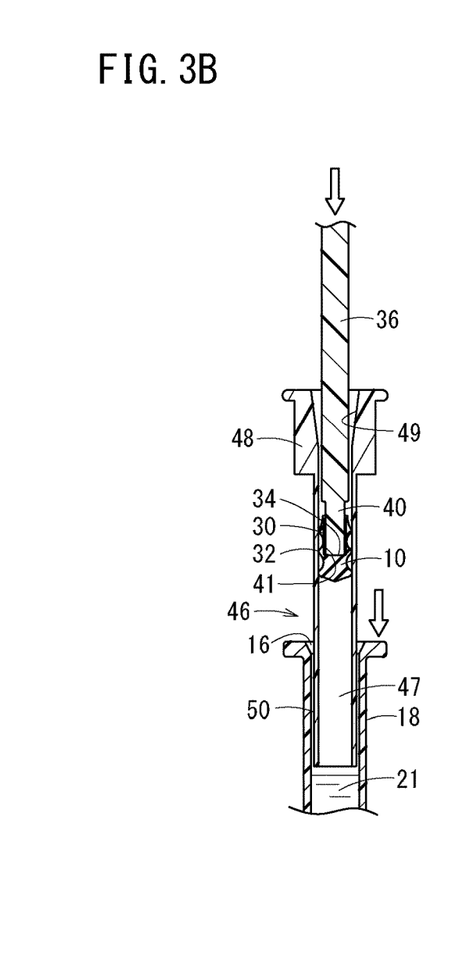
FIG. 3B is a second diagram describing the gasket insertion method according to the embodiment of the present invention.

As illustrated in FIG. 3B, in the present embodiment, the sleeve 46 is moved downward by the action of the first moving mechanism described above, and also the inserter 36 is moved downward by the action of the second moving mechanism described above. Thus, the sleeve 46 is inserted, through the base end opening section 16, up to a predetermined position inside the outer cylinder 18, and also the gasket 10 is pushed downward by the tip end section 40 of the inserter 36 and is inserted into the sleeve 46.

The gasket 10 is compressed inside the inner space 47, and is easily inclined due to large frictional resistance caused by elastic stress at the time of movement. In the present embodiment, at the time of the tip end section 40 of the inserter 36 pushing the gasket 10 downward, the tip end section 40 is inserted into the recessed section 30, and the flat tip end surface 41 of the tip end section 40 and the flat bottom surface 34 of the recessed section 30 come into contact with each other (see also FIG. 2). The gasket 10 is thereby relatively moved in the tip end direction inside the sleeve 46 in a state where the axis of the gasket 10 and the axis of the inserter 36 substantially coincide with each other or where the axes are substantially parallel to each other. Accordingly, the gasket 10 may be installed in parallel regardless of the frictional resistance at the time of movement.

At the time of insertion of the gasket 10 in the tip end direction inside the sleeve 46, the gasket 10 is pressed inward in the radial direction by the action of the tapered section 49 of the base section 48, and the diameter of the gasket 10 is reduced. Accordingly, the gasket 10 moves in the tip end direction inside the insertion section 50 of the sleeve 46 with its diameter reduced.

Figure 3C:
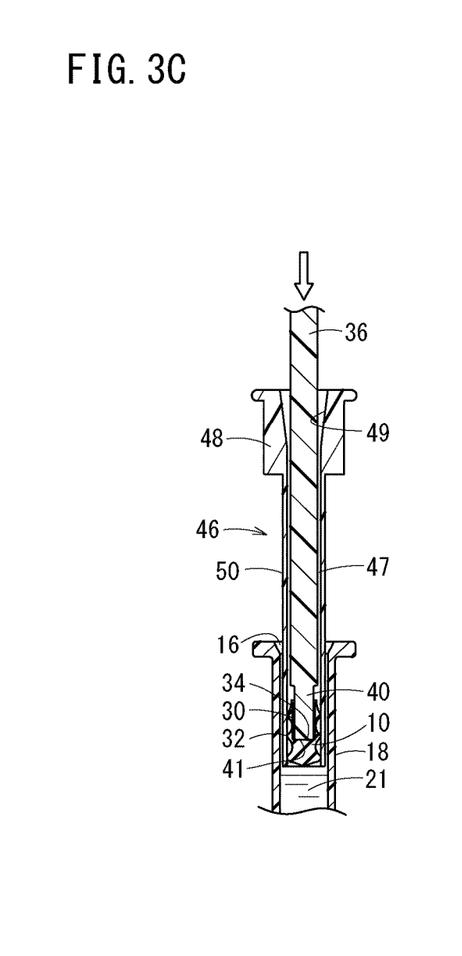
FIG. 3C is a third diagram describing the gasket insertion method according to the embodiment of the present invention.

Moreover, as illustrated in FIG. 3C, the gasket 10 is pushed to near the tip end of the sleeve 46 by the inserter 36. As described above, the outer diameter of the insertion section 50 of the sleeve 46 is smaller than the inner diameter of the outer cylinder 18, and thus a gap is formed between the outer circumferential surface of the insertion section 50 and the inner circumferential surface of the outer cylinder 18. Accordingly, the air between the tip end surface 28 of the gasket 10 and the liquid surface 21*a* of the drug solution 21 may escape to outside the outer cylinder 18 through the gap as the gasket 10 is moved downward inside the sleeve 46. The pressure inside the space between the tip end surface 28 of the gasket 10 and the liquid surface 21*a* of the drug solution 21 is thus be maintained at substantially the atmospheric pressure.

Figure 4A:
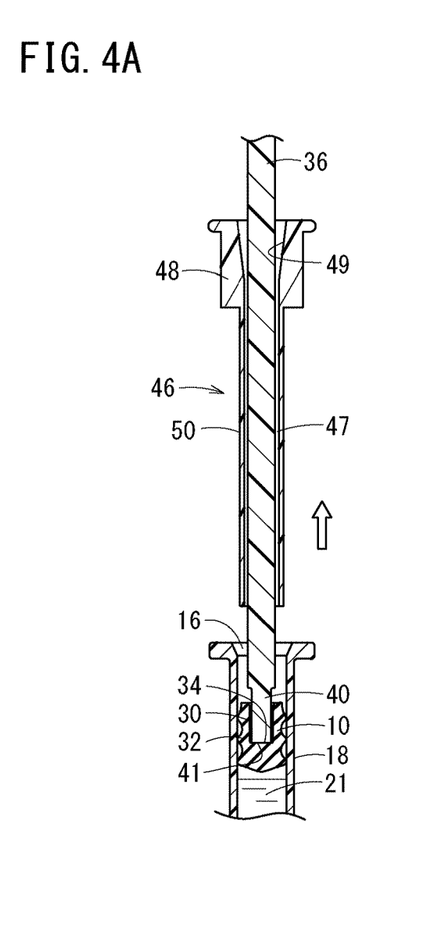
FIG. 4A is a fourth diagram describing the gasket insertion method according to the embodiment of the present invention.

Next, the gasket 10 is placed inside the outer cylinder 18 by relatively moving the inserter 36 in the base end direction while maintaining the relative positions of the outer cylinder 18, the gasket 10, and the sleeve 46 in the axial direction (an arrangement step). Specifically, as illustrated in FIG. 4A, only the sleeve 46 is moved upward by the action of the first moving mechanism so that the tip end section 40 of the sleeve 46 is pulled out from the base end opening section 16 of the outer cylinder 18. At this time, since the tip end surface 41 of the inserter 36 and the bottom surface 34 of the recessed section 30 of the gasket 10 are in contact with each other, upward movement (in the base end direction) of the gasket 10 is restricted by the inserter 36. Accordingly, as illustrated in FIG. 4A, when the sleeve 46 is moved upward, the gasket 10 is released inside the outer cylinder 18 from the tip end opening of the sleeve 46.

The diameter of the gasket 10 set free from the restriction in the radial direction by the sleeve 46 is increased due to elastic restoring force of the gasket 10, and the outer circumferential section of the gasket 10 comes into close contact with the inner circumferential surface of the outer cylinder 18. In the case of the present embodiment, the recessed section 30 of the gasket 10 is substantially column shaped, and the tip end section 40 of the inserter 36 which is also substantially column shaped is inserted in the inner circumferential section 31 with a relatively small gap, and thus the gasket 10 is supported by the columnar outer circumferential section. Accordingly, the gasket 10 may be stably held despite the motion in the sideways direction at the time of upward movement of the inserter 36 after the arrangement step and the simultaneous expansion of the gasket 10. A plurality of circular ribs 32 provided on the outer circumferential section of the gasket 10 thus come into close contact with the inner circumferential surface of the outer cylinder 18, thereby forming a liquid-tight seal.

In the state illustrated in FIG. 3C, which is immediately before release of the gasket 10 inside the outer cylinder 18, inclination of the gasket 10 with respect to the sleeve 46 is suppressed. That is, in the state in FIG. 3C, the axis of the gasket 10 and the axis of the sleeve 46 substantially coincide with each other or are substantially parallel to each other. Accordingly, the axis of the gasket 10 released from the sleeve 46 inside the outer cylinder 18 and arranged inside the outer cylinder 18 substantially coincides with the axis of the outer cylinder 18. That is, inclination of the axis of the gasket 10 with respect to the axis of the outer cylinder 18 is suppressed.

Figure 4B:
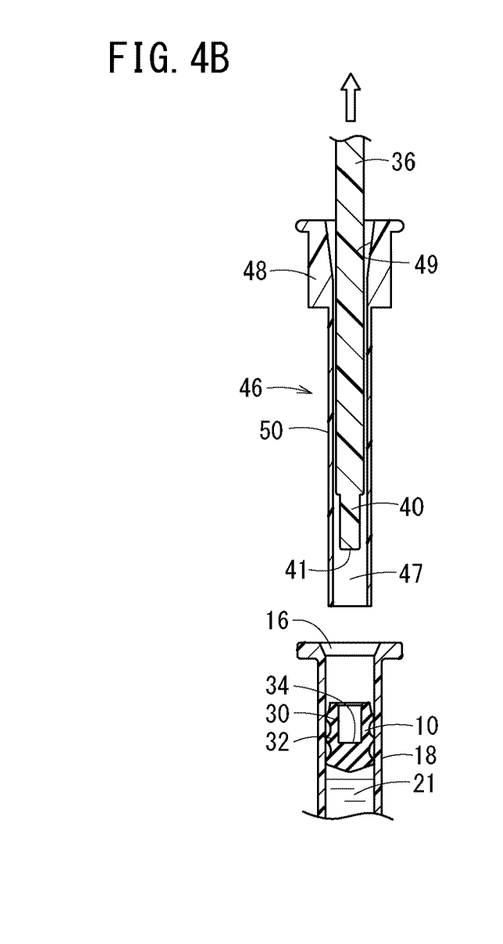
FIG. 4B is a fifth diagram describing the gasket insertion method according to the embodiment of the present invention.

When the gasket 10 is arranged inside the outer cylinder 18, the inserter 36 is then relatively moved in the base end direction with respect to the outer cylinder 18. Specifically, as illustrated in FIG. 4B, the inserter 36 is moved upward, and the inserter 36 is pulled out of the outer cylinder 18. Additionally, if, in FIG. 4A, the gasket 10 is already released inside the outer cylinder 18 from the tip end opening of the sleeve 46, the inserter 36 may be moved upward at the same time as the sleeve 46 is moved upward. In the case where the time lag until the movement of the inserter 36 is small, large-scale manufacturing may be efficiently performed.

The prefilled syringe 12 illustrated in FIG. 1 is manufactured in the manner described above.

As described above, according to the gasket insertion method and the gasket 10 according to the present embodiment, the bottom surface 34 of the recessed section 30 provided to the gasket 10 is flat, and the tip end surface 41 of the inserter 36 is also flat. Accordingly, when the gasket 10 is pushed by the inserter 36 and is inserted into the sleeve 46, the gasket 10 may be moved downward by a force that is uniform in the horizontal direction, and even if the frictional resistance between the gasket 10 and the inner wall of the inner space 47 is great, inclination of the gasket 10 with respect to the sleeve 46 may be suppressed. Therefore, the gasket 10 may be arranged inside the outer cylinder 18 in a state where the inclination of the gasket 10 with respect to the outer cylinder 18 is suppressed. And moreover, the gap between the recessed section 30 of the gasket 10 and the tip end section 40 of the inserter 36 is small and the gasket 10 is supported by the outer circumferential surface of the inserter 36. Therefore, the gasket 10 is stably held at the time of the sleeve 46 moving upward, and thus the gasket 10 may be held horizontally until it has expanded inside the outer cylinder 18. Inclination of the gasket 10 with respect to the outer cylinder 18 may be suppressed in this manner, and the circular ribs 32 may be brought into close, circumferentially uniform contact with the inner circumferential surface of the outer cylinder 18, and thus the outer appearance of the prefilled syringe 12 may be prevented from being impaired. Furthermore, since an increase in the sliding resistance between the gasket 10 and the outer cylinder 18 due to the inclination of the gasket 10 is suppressed, an increase in the resistance at the time of pushing the gasket 10 by a plunger in the tip end direction with respect to the outer cylinder 18 (pushing resistance) is suppressed. Accordingly, the operability of the prefilled syringe 12 at the time of use is not reduced. At the same time, the stability at the time of storing the drug solution 21 inside the outer cylinder 18 is increased.

In the case of the present embodiment, the inner diameter of the recessed section 30 provided to the gasket 10 is substantially constant along substantially the entire length in the depth direction. According to such a structure, the inner circumferential surface of the recessed section 30 whose inner diameter is constant in the depth direction is supported also by the outer circumferential surface of the tip end section 40 of the inserter 36. Inclination of the gasket 10 may be effectively suppressed at the time of insertion of the gasket 10 into the sleeve 46.

In the case of the present embodiment, the ratio of the inner diameter d of the recessed section 30 to the outer diameter of the gasket 10 (the outer diameter Dr1 of the circular rib 32) is 30% or more, and preferably, it is 40% or more, and the ratio of the outer diameter D of the tip end section 40 of the inserter 36 to the inner diameter d of the recessed section 30 is 60%, and preferably, it is 80% or more. According to such a structure, the tip end section 40 of the inserter 36 to be inserted in the recessed section 30 of the gasket 10 is relatively thick, and also the gap between the outer circumferential surface of the tip end section 40 of the inserter 36 and the inner circumferential surface of the recessed section 30 is small. Accordingly, inclination of the gasket 10 may be effectively suppressed at the time of insertion of the gasket 10 into the sleeve 46.

In the case of the present embodiment, the difference between the outer diameter Dr1 of the circular rib 32 and the outer diameter Dv1 of the valley section 44 is 0.7 mm or more, and preferably, it is 1 mm or more, or the ratio of the outer diameter Dv1 of the valley section 44 to the outer diameter Dr1 of the circular rib 32 is 90% or less, and preferably, it is 82% or less. According to such a structure, inclination of the gasket 10 may be effectively suppressed without increasing the sliding resistance between the gasket 10 and the outer cylinder 18.

Figure 5:
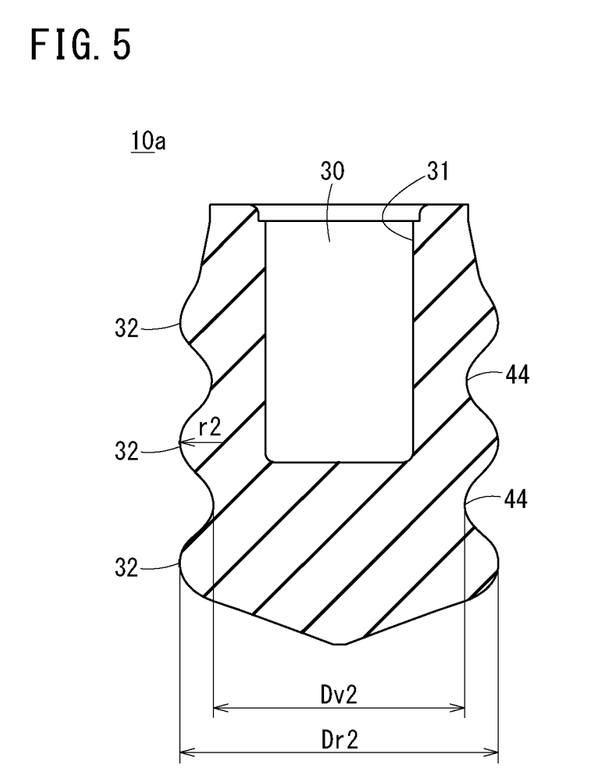
FIG. 5 is a longitudinal cross-sectional diagram illustrating a gasket having a different outer shape from the gasket illustrated in FIG. 2.

FIG. 5 is a longitudinal cross-sectional diagram illustrating a gasket 10*a* having a different outer shape from the gasket 10 described above. According to the gasket 10*a*, an outer diameter Dr2 of a circular rib 32 is 5.25 mm, and an outer diameter Dv2 of a valley section 44 is 4.4 mm. Accordingly, the ratio of the outer diameter Dv2 of the valley section 44 to the outer diameter Dr2 of the circular rib 32 is about 83.8%, and the difference between the outer diameter Dr2 of the circular rib 32 and the outer diameter Dv2 of the valley section 44 is 0.85 mm. Also, a curvature of radius r2 at a crown section of the circular rib 32 of the gasket 10*a* is about two times the curvature of radius r1 at the crown section of the circular rib 32 of the gasket 10.

According to the gasket 10 illustrated in FIG. 2, the sliding resistance with respect to the outer cylinder 18 may be reduced than for the gasket 10*a* illustrated in FIG. 5. This is because, when comparing the shapes of the circular ribs 32 of the gasket 10 and the gasket 10*a*, the circular rib 32 of the gasket 10 is smaller than the circular rib 32 of the gasket 10*a* in the axial and radial directions, and also with respect to volume. That is, since the circular rib 32 of the gasket 10 is smaller than the circular rib 32 of the gasket 10*a*, the contact pressure with respect to the inner circumferential surface of the outer cylinder 18 due to the elastic energy of the circular rib 32 in an elastically compressed state is smaller by this amount.

The present invention has been described above by citing a preferred embodiment, but the present invention is not limited to the embodiment described above, and it is needless to say that various modifications may be made within the spirit of the present invention.

What is claimed is:

1. A gasket insertion method for inserting a gasket into an outer cylinder of a pre-filled syringe, the method comprising:

providing the outer cylinder, which comprises:
an inner space filled with a drug solution,
an opening into the inner space at a base end of the outer cylinder, and
a cylinder tip section at a tip end of the outer cylinder opposed to the base end of the outer cylinder;
providing a gasket that comprises:
a recessed section,
an opening into the recessed section at a base end of the gasket, and
a flat bottom surface at a bottom of the recessed section;
providing an inserter having a tip end section and a flat tip end surface at a tip end of the inserter;
providing a sleeve having an opening at a tip end of the sleeve, the sleeve being configured to be inserted into the outer cylinder from the opening of the outer cylinder,
pushing the gasket into the sleeve by moving the inserter in a tip end direction with respect to the sleeve while the tip end section of the inserter is disposed in the recessed section and the flat tip end surface of a tip end section of the inserter abuts the bottom surface of the recessed section;
inserting the sleeve into the inner space of the outer cylinder through the opening of the outer cylinder while the tip end of the sleeve faces downward, and while the outer cylinder is held with the cylinder tip section of the outer cylinder facing downward, wherein the sleeve is inserted to an insertion position in which (i) the tip end of the sleeve is located proximate to a liquid surface of the drug solution, (ii) the gasket is located proximate to the tip end of the sleeve, and (iii) the sleeve and the gasket do not contact the drug solution; and
pushing the gasket out from the sleeve through the opening of the sleeve into the inner space of the outer cylinder by relatively moving the sleeve from the insertion position in a base end direction with respect to the outer cylinder while maintaining relative axial positions of the outer cylinder, the gasket, and the inserter, such that a liquid-tight seal is formed between an inner peripheral surface of the outer cylinder and an outer peripheral surface of the gasket.

2. The gasket insertion method according to claim 1, wherein an inner surface of the recessed section is cylindrical along substantially an entire length from the opening into the recessed section to the bottom of the recessed section.

3. The gasket insertion method according to claim 1, wherein:
a ratio of an inner diameter of the recessed section to an outer diameter of the gasket is 30% or more, and
a ratio of the outer diameter of the tip end section of the inserter to the inner diameter of the recessed section is 60% or more.

4. The gasket insertion method according to claim 1, wherein:
a plurality of circular ribs are located on an outer circumferential section of the gasket, the circular ribs being spaced apart from each other in an axial direction of the gasket, and
a difference between an outer diameter of the circular rib and an outer diameter of a valley section that is located between adjacent circular ribs is 0.7 mm or more, or a ratio of the outer diameter of the valley section to the outer diameter of the circular rib is 90% or less.

5. The gasket insertion method according to claim 2, wherein:

a plurality of circular ribs are located on an outer circumferential section of the gasket, the circular ribs being spaced apart from each other in an axial direction of the gasket, and a difference between an outer diameter of the circular rib and an outer diameter of a valley section that is located between adjacent circular ribs is 0.7 mm or more, or a ratio of the outer diameter of the valley section to the outer diameter of the circular rib is 90% or less.

6. The gasket insertion method according to claim 3, wherein:

a plurality of circular ribs are located on an outer circumferential section of the gasket, the circular ribs being spaced apart from each other in an axial direction of the gasket, and a difference between an outer diameter of the circular rib and an outer diameter of a valley section that is located between adjacent circular ribs is 0.7 mm or more, or a ratio of the outer diameter of the valley section to the outer diameter of the circular rib is 90% or less.

7. The gasket insertion method according to claim 4, wherein:

of the plurality of circular ribs, a circular rib that is farthest on a tip end side of the gasket is provided on the tip end side of the gasket relative to the bottom surface, and of the plurality of circular ribs, a circular rib that is farthest on a base end side of the gasket is provided on the base end side of the gasket relative to the bottom surface.

8. The gasket insertion method according to claim 5, wherein:

of the plurality of circular ribs, a circular rib that is farthest on a tip end side of the gasket is provided on the tip end side of the gasket relative to the bottom surface, and of the plurality of circular ribs, a circular rib that is farthest on a base end side of the gasket is provided on the base end side of the gasket relative to the bottom surface.

9. The gasket insertion method according to claim 6, wherein:

of the plurality of circular ribs, a circular rib that is farthest on a tip end side of the gasket is provided on the tip end side of the gasket relative to the bottom surface, and of the plurality of circular ribs, a circular rib that is farthest on a base end side of the gasket is provided on the base end side of the gasket relative to the bottom surface.

10. A gasket for insertion in an outer cylinder in a slidable manner, the gasket comprising:

a gasket main body including a tip end and a base end;

a recessed section;

an opening into the recessed section at the base end of the gasket main body;

a flat bottom surface at a bottom of the recessed section; and a plurality of circular ribs that are located on an outer circumferential section of the gasket main body, the circular ribs being spaced apart from each other in an axial direction of the gasket main body, wherein an inner surface of the recessed section is cylindrical along substantially an entire length from the opening to the flat bottom surface, wherein an inner surface of the recessed section is cylindrical along substantially an entire length from the opening into the recessed section to the bottom of the recessed section, wherein a difference between an outer diameter of the circular rib and an outer diameter of a valley section that is located between adjacent circular ribs is 0.7 mm or more, or a ratio of the outer diameter of the valley section to the outer diameter of the circular rib is 90% or less, and wherein a ratio of the inner diameter of the recessed section to the outer diameter of the circular ribs is 30% or more.

11. The gasket according to claim 10, wherein:

of the plurality of circular ribs, a circular rib that is farthest on a tip end side of the gasket is provided on the tip end side of the gasket relative to the bottom surface, and of the plurality of circular ribs, a circular rib that is farthest on a base end side of the gasket is provided on the base end side of the gasket relative to the bottom surface.

* * * * *